(12) United States Patent
Gebski et al.

(10) Patent No.: US 9,791,416 B2
(45) Date of Patent: Oct. 17, 2017

(54) FURNACE STRUCTURAL INTEGRITY MONITORING SYSTEMS AND METHODS

(71) Applicant: Hatch Ltd., Mississauga (CA)

(72) Inventors: Pawel Boleslaw Gebski, Mississauga (CA); Afshin Sadri, Woodbridge (CA); Wai-Lai Ying, Mississauga (CA)

(73) Assignee: Hatch Ltd., Mississauga (CA)

( * ) Notice: Subject to any disclaimer, the term of this patent is extended or adjusted under 35 U.S.C. 154(b) by 351 days.

(21) Appl. No.: 14/081,327

(22) Filed: Nov. 15, 2013

(65) Prior Publication Data

US 2014/0123758 A1  May 8, 2014

Related U.S. Application Data

(63) Continuation of application No. PCT/CA2012/000526, filed on May 22, 2012.

(60) Provisional application No. 61/488,386, filed on May 20, 2011.

(51) Int. Cl.
| | |
|---|---|
| *G01N 29/14* | (2006.01) |
| *G01N 29/44* | (2006.01) |
| *F27B 3/28* | (2006.01) |
| *F27D 21/00* | (2006.01) |

(52) U.S. Cl.
CPC ............. *G01N 29/14* (2013.01); *F27B 3/28* (2013.01); *F27D 21/0021* (2013.01); *G01N 29/4427* (2013.01)

(58) Field of Classification Search
CPC ............. G01N 29/14; G01N 29/4427; F27D 21/0021; F27B 3/28
USPC .................................. 73/587, 597, 598, 602
See application file for complete search history.

(56) References Cited

U.S. PATENT DOCUMENTS

| | | | |
|---|---|---|---|
| 4,207,771 A | 6/1980 | Carlos et al. | |
| 5,351,655 A | 10/1994 | Nuspl | |
| 5,557,631 A | 9/1996 | Bulat et al. | |
| 6,386,038 B1 * | 5/2002 | Lewis et al. | 73/587 |
| 6,603,795 B2 | 8/2003 | Ma et al. | |
| 7,665,362 B2 | 2/2010 | Sadri | |
| 8,919,202 B2 * | 12/2014 | Keely et al. | 73/649 |

(Continued)

FOREIGN PATENT DOCUMENTS

| | | |
|---|---|---|
| EP | 589544 B1 | 1/2002 |
| JP | 58187853 A | 11/1983 |

(Continued)

OTHER PUBLICATIONS

US 6,519,274, 02/2003, Ma et al. (withdrawn)

(Continued)

*Primary Examiner* — Paul West
*Assistant Examiner* — Xin Zhong
(74) *Attorney, Agent, or Firm* — Bereskin & Parr LLP/S.E.N.C.R.L., S.r.l.

(57) ABSTRACT

Various systems and method for acoustic monitoring of smelting furnaces and similar devices are disclosed. Acoustic sensors (and optionally other sensors) are mounted to the furnace. Acoustic emission events generated in the furnace are analyzed to identify conditions that exceed one or more thresholds. The location of acoustic emissions may be identified and reported. Output signals may be generated in response to acoustic emissions. The location of acoustic emissions may be used to identify the location of potential failures in the furnace.

29 Claims, 7 Drawing Sheets

(56) References Cited

U.S. PATENT DOCUMENTS

| | | | |
|---|---|---|---|
| 2004/0177692 A1* | 9/2004 | Sadri et al. | 73/602 |
| 2006/0186585 A1* | 8/2006 | Sadri | 266/78 |
| 2007/0095138 A1* | 5/2007 | El-Bakry et al. | 73/583 |
| 2008/0307926 A1 | 12/2008 | Matschullat | |
| 2009/0070048 A1 | 3/2009 | Stothers et al. | |
| 2010/0135119 A1 | 6/2010 | Paget | |

FOREIGN PATENT DOCUMENTS

| | | | |
|---|---|---|---|
| JP | 7145410 A | 6/1995 | |
| WO | 2006/024164 A3 | 3/2006 | |
| WO | 2006/089414 A1 | 8/2006 | |
| WO | 2012/159208 A1 | 11/2012 | |

OTHER PUBLICATIONS

"Dynamic monitoring of blast furnace plant", Office for Official Publicaitons of the European Communities, Luxembourg. XP00273622, ISBN: 92-828-1699-0.*

"Crack classification in concrete based on acoustic emission", Kentaro Ohno, 2010 Published by Elsevier Ltd.*

Document relating to EP Application No. 12789391.5, dated Mar. 10, 2015 (Extended European Search Report).

"Dynamic Monitoring of Blast Furnace Plant", Office for Official Publications of the European Communities, Luxembourg, XP002736221, ISBN: 92-828-1699-0, pp. 1-24.

Document relating to PCT Application No. PCT/CA2012/000526, dated Nov. 29, 2012 (International Search Report).

Document relating to PCT Application No. PCT/CA2012/000526, dated Nov. 20, 2013 (International Written Opinion of the Search Authority).

Document relating to PCT Application No. PCT/CA2012/000526, dated Nov. 20, 2013 (International Preliminary Report on Patentability).

Gang Peng Et al. "Design of 3-D mouse using ultrasonic distance measurement", Proc. SPIE 4077, International Conference on Sensors and Control Techniques (ICSC 2000), pp. 226-229, May 9, 2000. DOI: 10.1117/12.385576 XP055362504. ISSN: 0277-786X, ISBN: 978-1-5106-0753-8. Available Online: http://proceedings.spiedigitallibrary.org/proceeding.aspx?articleid=911270.

* cited by examiner

FURNACE STRUCTURAL INTEGRITY MONITORING SYSTEMS AND METHODS

This application is a continuation of International Application No. PCT/CA2012/000526 filed May 22, 2012, which claims the benefit of U.S. Provisional Application No. 61/488,386 filed May 20, 2011.

FIELD

The described embodiments relate to a system and method for monitoring the structural integrity and physical deformation of a metallurgical furnace.

BACKGROUND

A typical metallurgical furnace is a container having sidewalls with a multi-layer construction. The outer layer is typically a steel shell provided for structural support. The inner layer includes a refractory lining, constructed from one or more layers of refractory bricks, that is provided to shield the outer steel shell from molten materials and aggressive chemicals inside the furnace. In some furnaces, a cooling layer is also provided between the outer steel shell and the refractory lining to prevent excessive heat transfer from the refractory lining to the outer steel shell. In some furnace designs, the layers of brick and/or cooling elements are set in place with a soft sand-like material that solidifies during the operation of the furnace.

During the operation of a metallurgical furnace, the refractory lining can be deteriorated by mechanical and thermal stress in addition to chemical degradation resulting in a loss of overall refractory lining thickness. As the refractory lining deteriorates molten materials and aggressive chemicals penetrate into widening spaces in and/or between refractory bricks leading to delamination (i.e. separation) of the layers in the refractory lining. Such delamination can exert expansive stresses on the outer steel shell, and may cause local deformation of the steel shell. Deterioration of the refractory lining can also lead to structural failures that may cause the outer steel shell to be exposed to molten materials and aggressive chemicals inside the furnace.

Moreover, if the molten materials and aggressive chemicals reach the outer steel shell there is an imminent risk of severe injury to personnel working near the furnace, because the outer steel shell is typically not capable of reliably holding back the molten materials and aggressive chemicals inside the furnace. Loss of heat transferability and conductivity are also known to occur as a result of the deterioration of the refractory lining, both of which may contribute to deformation and failure of the steel shell.

Another mode of refractory lining deterioration, common in furnaces that include water-cooled elements, is hydration of the refractory lining. Under certain temperatures, water that has leaked from a cooling element can react with the refractory bricks causing expedited deterioration of the refractory lining. In particular, magnesia (MgO) based refractory bricks are susceptible to this mode of failure. Expansion of the refractory lining caused by hydration can exert increased expansive pressures on the steel shell, and may contribute to local deformation of the shell.

It is desirable to monitor the structural integrity of the furnace, and particularly the outer steel shell, in order to help predict the timing and location of shell ruptures. Making a reliable and accurate assessment of the condition of the steel shell is difficult to do without first emptying the furnace and shutting down the industrial process in which the furnace is involved. Shutting down a metallurgical furnace for routine inspection is costly and operators try to make use of inspection methods that can be employed while the furnace is operating. However, the hostile working environment in which a furnace is typically used skew the measurements made. For example, extremely high temperatures in the furnaces, vibrations, ambient noise, dust, and electrical and mechanical hazards are known to distort the structural integrity measurements generated by the previously known inspection methods. Conventional deformation monitoring tools, such as strain gauges, can be useful, but can only measure deformation in the vicinity in which they are installed. Further, conventional strain gauges are generally unable to differentiate between elastic and plastic deformation of the outer shell.

A systematic method monitoring the structural integrity of the steel shell and identifying the beginning cracks and other structural defects in real-time has not been developed. As a result, operators are forced to shut down and cool furnaces in order to check the shell integrity from time-to-time, and may have little or no warning of an impending shell rupture which can result in the leakage of molten metal from the furnace into the surrounding environment (a run-out).

SUMMARY

In a first aspect, various embodiments provide an acoustic emission monitoring system for monitoring structural integrity of a furnace having a furnace shell, the system comprising: a controller; and a plurality of acoustic emission sensors mounted to the furnace shell and to the controller to provide electric signals corresponding to acoustic emission (AE) events generated in the furnace to the controller.

In some embodiments, at least some of the sensors are coupled to the controller through a preamplifier.

In some embodiments, at least some of the sensors are removably mounted to the furnace shell.

In some embodiments, at least some of the sensors are magnetically mounted to the furnace shell.

In some embodiments, at least some of the sensors are permanently mounted.

In some embodiments, at least some of the sensors are mounted to the furnace shell in a predetermined mounting pattern.

In some embodiments, at least some of the sensors are mounted to the furnace shell in positions corresponding to one or more furnace components.

In some embodiments, the spacing of at least some of the sensors mounted on the furnace shell is determined by one or more factors selected from the following list of factors: properties of some or all of the sensors; the resolution of some of all of the sensors; the number of sensors used; the location of furnace components; and the size of the furnace.

In some embodiments, at least some of the sensors are sensitive to acoustic emissions having a frequency higher than a selected threshold.

In some embodiments, the controller includes a filtration module to filter the electric signals.

In some embodiments, the filtration module filters out signals below a selected threshold.

In some embodiments, the threshold is selected from the group consisting of: an operating threshold AE value; a warning AE threshold value, an alarm AE threshold value and a shutdown AE threshold value.

In some embodiments, the system includes sensors of different types.

In some embodiments, the controller includes an output module for providing one or more output signal corresponding to the electric signals.

In some embodiments, an output signal is provided when the intensity of AE events detected by at least one of the sensors exceeds a threshold.

In some embodiments, the threshold is selected from the group consisting of: an operating threshold AE value; a warning AE threshold value, an alarm AE threshold value and a shutdown AE threshold value.

In some embodiments, at least one of the output signals is selected from the group consisting of: warning signals, alarm signals, control signals, sensor control signals and feedback signals.

In some embodiments, the controller includes a display apparatus for providing information relating to the electric signals.

In some embodiments, the controller includes a location module for estimating the location of the origin of an acoustic emission event.

In another aspect, some embodiments, provide a method of monitoring the structure of a furnace, the method including: mounting a plurality of acoustic emission sensors to the furnace shell; receiving, from at least one of the acoustic emissions sensors, electric signals corresponding to an acoustic emission event generated in the furnace; and analyzing the electric signals.

In some embodiments, the method includes positioning at least some of the sensors in a predetermined mounting pattern.

In some embodiments, the method includes positioning at least some of the sensors in positions corresponding to one or more furnace components.

In some embodiments, the method includes spacing the sensors mounted on the furnace shell based on one or more factors selected from the following list of factors: properties of some or all of the sensors; the resolution of some of all of the sensors; the number of sensors used; the location of furnace components; and the size of the furnace.

In some embodiments, the method includes filtering out acoustic emissions that are identified by fewer than a selected number of the sensors.

In some embodiments, the method includes filtering out acoustic emissions corresponding to normal operating noises of the furnace.

In some embodiments, the controller includes a display apparatus for providing information relating to the electric signals.

In some embodiments, the method includes estimating the location of the origin of an acoustic emission event.

In some embodiments, the method includes identifying one or more pre-cursor AE events.

In some embodiments, the method includes applying a speed wave correction based on the operating temperature of a furnace to refine the estimated location of the origin of an acoustic emission event.

In some embodiments, the method includes providing an output identifying the estimated location of the origin of an acoustic emission event.

BRIEF DESCRIPTION OF THE DRAWINGS

For a better understanding of the applicant's teachings described herein, reference will now be made, by way of example only, to the accompanying drawings which show at least one exemplary embodiment, and in which.

For simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

Various apparatuses or processes are described below to provide an example of an embodiment of each claimed invention. No embodiment described below limits any claimed invention and any claimed invention may cover processes or apparatuses that are not described below. The claimed inventions are not limited to apparatuses or processes having all of the features of any one apparatus or process described below or to features common to multiple or all of the apparatuses described below. It is possible that an apparatus or process described below is not an embodiment of any claimed invention. Any invention disclosed in an apparatus or process described below that is not claimed in this document may be the subject matter of another protective instrument, for example, a continuing patent application, and the applicants, inventors or owners do not intend to abandon, disclaim or dedicate to the public any such invention by its disclosure in this document.

Run-outs are undesirable but common occurrences with operating metallurgical furnaces. A run-out occurs when the molten contents of the furnace leaks into the surrounding environment. Run-outs can result in costly down-time for the furnace, and can pose a safety hazard to operators working in the vicinity of the furnace.

Some run-outs can be caused by flaws in or between the refractory lining of a furnace, which allow molten metal to seep through the refractory layers and contact the steel outer shell of the furnace. Refractory flaws can be caused by extensive wear of internal refractory lining, or hydration and physical/chemical deformation and weakening of the refractory lining or through a discontinuity in the lining. The Applicant has discovered that these mechanisms causing a run-out, can produce acoustic emissions and can result in furnace shell deformations.

Combinations of systems and methods for measuring elastic and plastic deformation of the furnace shell, detecting micro cracking and cracking of the furnace shell, detecting refractory displacements and formation of discontinuities resulting in run-outs and detecting the refractory wear can be used to help facilitate the structural integrity monitoring of metallurgical furnaces. Such systems may allow timely application of preventive measures or safety procedures, if required, before the damage of the furnace becomes severe and/or results in a run-out.

A structural integrity monitoring system can be used to monitor the structural integrity of furnace. Optionally, the structural integrity monitoring system can be used to monitor the condition of the furnace in real-time. The structural integrity monitoring system can be configured to use a plurality of different types of sensors, either individually or in combination. Suitable types of sensors can include, for example, acoustic sensors, vibration sensors, strain gauges, optical sensors and temperature sensors. In some instances it may be useful to include multiple different types of sensors within an integrity monitoring system to help facilitate the collection of multiple types of data. Optionally, this combination of data can be processed using a common system controller. For simplicity, an example of a structural integrity monitoring system described below is described as having a single type of acoustic emission sensor, however other embodiments of the integrity monitoring system may include a plurality of different sensor types.

Acoustic emission testing is a method for monitoring the condition of materials deforming under an externally and/or internally applied stress. Acoustic emissions (AE) may be defined as a transient elastic waves generated by the rapid release of energy within a material when the material is yielding or plastically deforming. Acoustic emission sensing or monitoring equipment can "listen" to the sounds of cracks growing, fibres breaking and many other modes of active damage in the stressed material. By monitoring AE signals from a given structure, small-scale damage to the structure may be detectable before a larger structural failure occurs. Multi-sensor AE systems can also be used to locate the origin of a crack (or other such mechanical failure) and predict the direction of crack propagation. When used in this manner, AE can be used as a non-destructive testing or monitoring technique to find defects, for example, during structural proof tests and plant operation.

The Applicant has discovered that an AE monitoring system can be configured to monitor the structural integrity of a smelting furnace.

Conventional strain gauge measurement techniques are capable of detecting physical expansion in the outer shell of a smelting furnace. However, known strain gauge base systems, relying primarily on dimensional changes in the material, cannot distinguish between reversible elastic deformation and potentially problematic plastic deformation in a material. Unlike strain gauge based systems, the Applicant's AE monitoring systems can be used to detect the stress waves generated by a rapid release of energy in a material, which usually accompanies plastic deformation. When undergoing reversible, elastic deformation, the internal structure of a material remains generally intact, and releases very little, if any acoustic emissions.

By monitoring acoustic emissions generated within a material, an AE monitoring system can be capable of identifying the transition from reversible to irreversible deformation in a material, and detecting active flaws in materials such as crack growth (including microcrack formation and growth).

The use of a plurality of sensors, for example arranged in sensors' arrays to define sensing regions, may help facilitate AE origin location. Identifying the source of the origin of AE signals can help identify areas of stress concentration in the material, which may lead to the formation of larger cracks and other defects. Locating the portions of the material that have undergone significant plastic deformation may help identify portions of the material that may be more likely to fail, and that may be inspected and/or repaired before failure.

Figure 1:
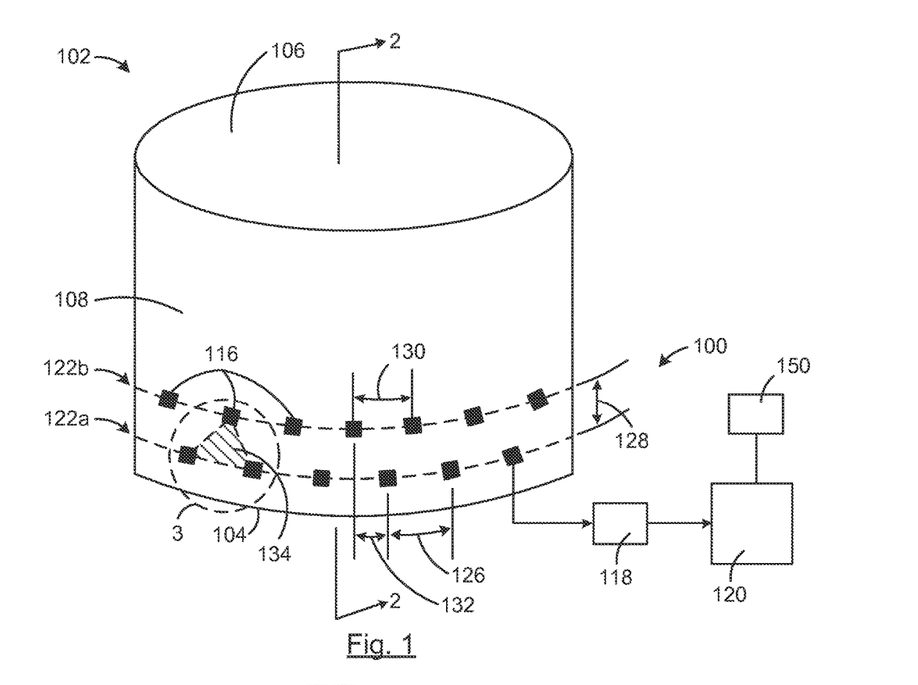
FIG. 1 is a schematic representation of an Acoustic Emission (AE) monitoring system installed on a metallurgical furnace.
Figure 2:
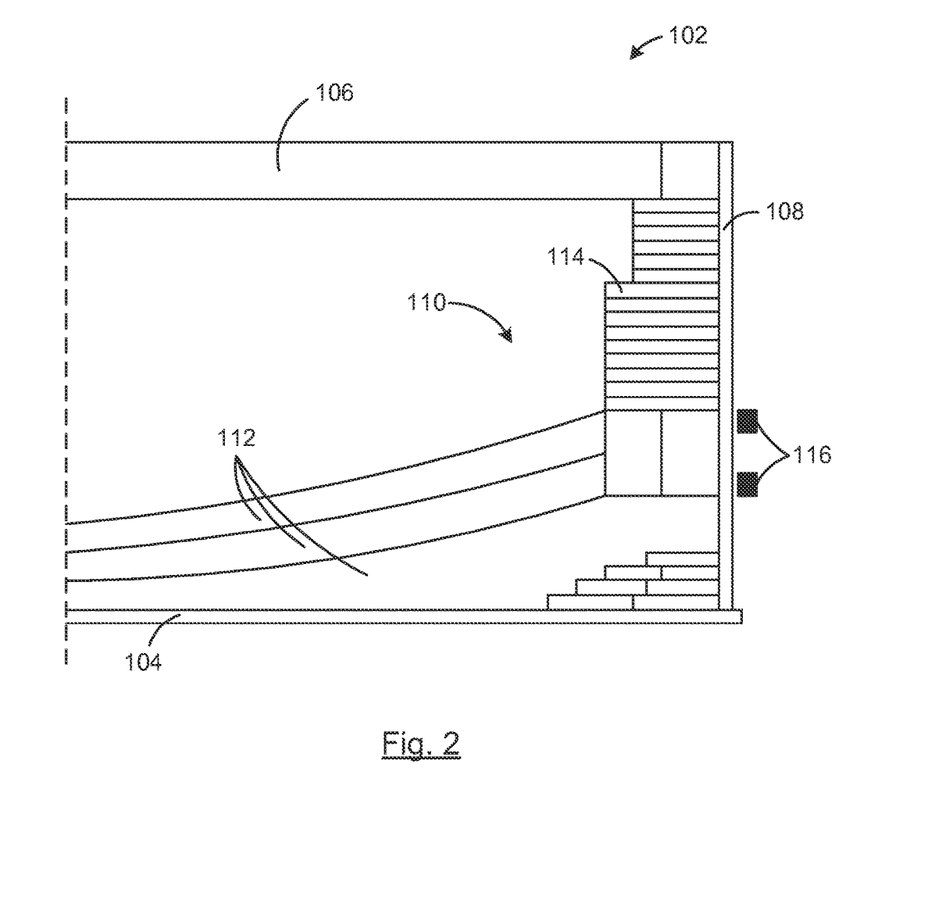
FIG. 2 is a partial cross-sectional view of the furnace of FIG. 1, taken along line 2-2.

Referring to FIGS. 1 and 2 an AE monitoring system 100 is installed on a metallurgical furnace 102 and is configured to monitor the structural integrity of the furnace.

In the illustrated example, the furnace 102 is an electric circular furnace that includes a bottom plate 104, a roof 106 and an outer shell 108. The outer shell 108 can be formed from any suitable material, including steel. The interior of the furnace 102 is lined with refractory material 110. Refractory material may help insulate the bottom plate 104 and outer shell 108 from the molten metal that can be contained in the furnace. In the illustrated example, the furnace 102 includes multiple hearth refractory layers 112 and wall refractory material 114.

Acoustic emissions may be generated by a plurality of sources within the furnace 102, including, for example, deformation and cracking of the outer shell 108, erosion of refractory material 110, movement of refractory material relative 110 to the outer shell 108, leaks in cooling water systems and electrode arcing.

The AE monitoring system 100 includes a plurality of AE sensors 116 mounted to the furnace 102. In the illustrated example, the AE monitoring system includes sixteen AE sensors 116 mounted on the outer shell 108 of the furnace 102. Optionally, the plurality of AE sensors 116 can be detachably mounted to the furnace outer shell 108 using a suitable detachable connecter, including, for example, a magnet. Alternatively, some or all of the AE sensors 116 can be permanently mounted furnace outer shell 108. The AE sensors 116 are operable to convert acoustic emissions generated within the furnace into corresponding electrical signals.

Each AE sensor 116 is linked to a corresponding AE preamplifier 118. For simplicity, only a single AE preamplifier 118 is illustrated in FIG. 1, however, a corresponding AE preamplifier 118 can be connected to each AE sensor 116. The AE preamplifiers 118 are configured to receive the corresponding electrical signals from the AE sensors 116 and to transmit an amplified electrical signal to a controller 120. The plurality of AE preamplifiers 118 are communicably linked to the controller 120, using a plurality of suitable data cables. In the illustrated example, the controller 120 is a computer. Alternatively, the controller 120 can be any suitable apparatus, including, for example a PLC.

Optionally, instead of being provided as separate components, the AE preamplifiers 118 may be integrated into the AE sensors 116, or the controller 120, as opposed to be provided as a separate component.

Optionally, the AE sensors 116, AE preamplifiers 118, controller 120, cables and any other system components can be thermally shielded to help protect the system components from the heat of the furnace.

Figure 3:
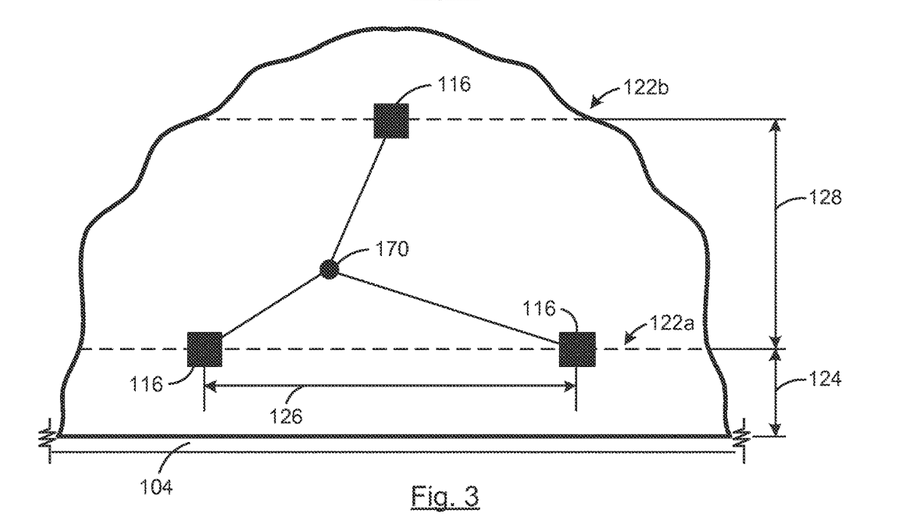
FIG. 3 is an enlarged view of region 3 of the furnace of FIG. 1.

Referring also to FIG. 3, the plurality of AE sensors 116 can be mounted to the outer shell 108 in a predetermined mounting pattern. In the illustrated example, the sixteen AE sensors 116 are mounted to the furnace outer shell 108 in two generally linear rows 122a, 122b. A first row 122a of AE sensors 116 is located at a first height 124 above the bottom plate 184 of the furnace 102. The height of the first row 122b can be selected based on a plurality of factors, including, for example, the configuration furnace and the location of furnace components (such as tapholes, stiffening layers, refractory layers, etc.). In the illustrated example, the first row of sensors 122a is positioned approximately one hundred fifty millimeters above the bottom plate 104 of the furnace 102.

The plurality of AE sensors 116 in the first row 122a are laterally offset from each other by a first lateral spacing distance 126. The first lateral spacing distance 126 can be selected based on a plurality of factors, including, for example, the AE sensor 116 properties (such as sensor resolution), the number of AE sensors 116 used, the location of furnace structural features (such as tapholes, stiffening elements, etc.) and the size of the furnace outer shell 108. In the illustrated example, the first lateral spacing distance 126 is approximately nine thousand millimeters. Using this lateral spacing distance 126 enables the plurality of AE sensors 116 in the first row 122a to be generally equally spaced around the perimeter of the furnace outer shell 108. Alternatively, the lateral spacing distance 126 between AE sensors 116 in the first row 122a need not be constant around the perimeter of the furnace 102.

A second row 122b of AE sensors 116 is positioned above the first row 122a and is offset from the first row 122a by a vertical offset distance 128. In the illustrated example, the vertical offset distance 128 is less than the first lateral spacing distance 126, and is approximately twelve hundred millimeters. Optionally, the vertical offset distance 128 can be between about five and about three thousand millimeters.

The AE sensors 116 in the second row 122b are offset from each other by a second lateral spacing distance 130. Optionally, as illustrated, the second lateral spacing distance 130 can be generally equal to the first lateral spacing distance 126.

Optionally, the AE sensors 116 in the second row 122b can be laterally offset from the AE sensors 116 in the first row 122a by a row lateral offset distance 132. In the illustrated example, the row lateral offset distance 132 is approximately half of the first lateral spacing distance 126.

Referring to FIGS. 1 and 3, in the illustrated configuration, each group of three, laterally adjacent AE sensors 116 (including sensors from both rows 122a, 122b) defines a generally triangular sensor region 134, illustrated using cross-hatching in FIG. 1. Optionally, the plurality of AE sensors 116 can be positioned in another pattern to form differently shaped sensor regions.

The AE sensors 116 can be any suitable type of AE sensor that can withstand the operating environment of the furnace 102. The operating frequency range of the AE sensors 116 can be selected so that it includes the expected acoustic emission frequencies of the furnace components, which can be, for example, between about 20 kHz and about 120 kHz. In some instances, relevant acoustic emission frequencies can be between about 60 kHz and about 80 kHz, or greater than 120 kHz. In the illustrated example, the sensors are model R6a—60 kHz piezoelectric resonant AE sensors, having an operating frequency range of about 35-100 kHz and an operating temperature range of about −65 to 175 degrees Celsius.

If the AE monitoring system 100 is intended to monitor only a portion of the acoustic emissions generated within the furnace 102 (for example acoustic emissions generated by changes in refractory 110 condition and/or plastic deformation in the outer shell 108), acoustic emissions generated by other sources can be separated out when the emissions are processed by the controller 120.

For example, relatively low frequency emissions generated by electrode arcing, which may be about 50 kHz, can be filtered out using a filtration module in the controller 120 (FIG. 4), which may include, for example, a high pass filter. Other types of normal operating noises may be identified and removed using pattern recognition software, which may also be provided in the filtration module or other portion of the controller 120.

Examples of such irrelevant acoustic signals may include mechanical noise, cooling water flow, furnace start-up sounds and tapping or lancing sounds. Irrelevant acoustic emissions, and other unwanted system noise, can be eliminated using one or more filters in the filtration module and/or by the use of supplemental "guard sensors" to help filter out or block the irrelevant signals.

Optionally, the AE sensors 116 can be selected so that the lower end of their operating frequency range (for example about 35 kHz) is higher than the expected range of frequencies that are produced using traditional reflection-based acoustic monitoring or ultrasonic testing systems (for example sound waves generated by hammers, strikers or other mechanical impacts that are expected to be between about 2 kHz and about 25 kHz). Selecting the AE sensor frequency range in this manner may help reduce the detection of relatively low frequency, unwanted and/or interfering sound waves via the AE sensors.

Optionally, all of the AE sensors 116 can be identical. Alternatively, the plurality of AE sensors 116 can include more than one type of AE sensor.

Figure 4:
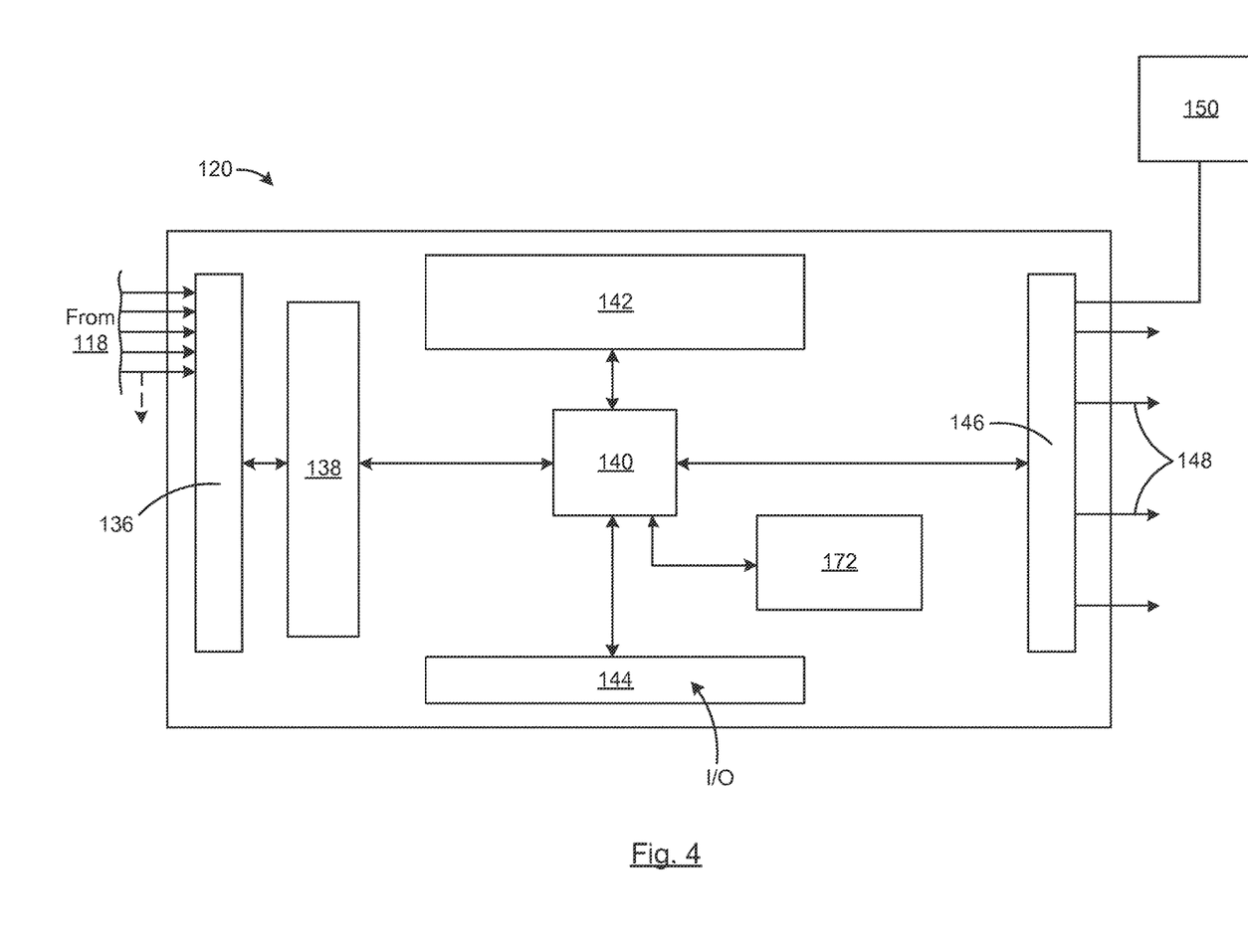
FIG. 4 is a schematic diagram of an example of a controller for an AE monitoring system.

Referring to FIG. 4, one example of the controller 120 includes an input module 136, a filtration module 138, a processor 140, a memory module 142, an operator I/O module 144 and an output module 146.

The input module 136 can be any suitable module that can be configured to receive electric signals from the plurality of AE preamplifiers 118, and transfer the signals to another controller 120 component. The input module 136 can be a multi-channel input module and can include an analogue to digital converter and other suitable components.

The filtration module 138 can include a combination of hardware and software components that can be configured to help filter signal noise and standard operating sounds from the AE signals detected by the AE sensors 116. The filtration module can include, for example, high pass, low pass and/or band pass filters and pattern recognition software components.

The processor 140 is linked to a plurality of other controller components, and can be any suitable processor.

The memory module 142 is configured to store system reference values, such as AE threshold values (as explained below), and can be queried by the processor 140. The memory module 142 can also store a variety of other software modules, including operating systems and sensor interface software.

The operator I/O module 144 is configured to enable a system operator to engage the AE monitoring system 100, for example to modify the operating parameters of the AE monitoring system 100. The I/O module 144 can include physical and graphical interface components, including, for example a keyboard, a mouse, a touchscreen and a display monitor.

The output module 146 is linked to the processor 140 and is operable to generate and output a variety of output signals 148. The output signals 148 can include a variety of signals, including, for example, warning signals, alarm signals, control signals (for example to control one or more functions of the furnace 102), sensor control signals and feedback signals.

The AE monitoring system 100 can also include a display apparatus 150. The display apparatus can be operable to provide information to a system operator. The display apparatus can include visual transducers (including for example display screens, lights and gauges), audible transducers (including, for example, horns, bells and sirens) and any combination thereof.

In use, the AE monitoring system 100 is used to monitor the acoustic emissions generated by the furnace 102 and to detect the occurrence of one or more AE events. An AE event is an acoustic emission that is related to, or may affect, the structural integrity of the furnace (e.g. emissions caused by plastic deformation of the outer shell and/or changes in the condition of the refractory), as opposed to the normal operating sounds and noises of the furnace.

AE activity in the furnace 102 can be measured by the number of AE events detected. AE intensity can be measured by magnitude of the AE event signal parameters (e.g. energy, amplitude, duration, rise time, etc.). Monitoring of both AE activity and AE intensity may be used to help identify changes in structural integrity.

The AE monitoring system 100 can be configured to continuously monitor the acoustic emissions from the furnace 102, in real time, and can generate warning or alert outputs if changes in structural integrity are detected.

In some instances, the plurality of AE sensors 116 may detect other acoustic signals that are generally irrelevant to the structural integrity of the furnace outer shell, and are not considered to be AE events.

Referring again to FIG. 3, in the illustrated example, the controller 120 is configured such that it will only recognize an acoustic emission as an AE event if the acoustic signal is detected by at least three AE sensors 116 on the outer shell 108. Detecting an AE event with at least three AE sensors may help facilitate triangulation of the origin of the AE event (represented graphically by point 170) based on, for example, the differences in times of arrival measured for each AE sensor 116. This configuration may also help filter out a portion of the noise-related or weak signals, if such signals are not detected by at least three AE sensors 116. The location of the origin 170 of the AE event relative to the AE sensors 116 can be converted into a physical location on the furnace 102 using the known locations of the AE sensors. Optionally, the controller 120 can include a location module 172 to calculate the location of the origin 170 of an AE event relative to the at least three AE sensors 116.

Identifying the origin 170 of the AE events generated on or within the outer shell 108 and/or refractory material 110 may help a user locate regions on the furnace 102 that are experiencing relatively high amounts of local plastic deformation, refractory wear or other structural changes. Identifying the location of such regions may help facilitate increased inspection and/or maintenance of such regions.

The operating temperature of the furnace 102 can affect the AE (i.e. stress wave) velocity in the refractory materials 110 and the outer shell 108. Once the furnace 102 is in operation, the wave speed correction due to temperature factor will be taken into consideration, for example using a thermal correction factor, to help facilitate accurate origin 170 location using triangulation. One example of such a thermal correction procedure is outlined in PCT publication WO 2006/089414 (Sadri et al.), the entirety of which is incorporated herein by reference.

The AE monitoring system 100, using the plurality of AE sensors 116, can also be configured to monitor the refractory wear. Positioning the AE sensors 116 in the predetermined array pattern (or alternatively another pattern such as a grid including multiple rows and columns) may help facilitate both the triangulation and zonal location of the origins 170 of the AE events generated by, or indicative of, refractory wear.

Ultrasonic wave velocity measurements may also be used in conjunction with active AE measurements. Ultrasonic wave measurements may help calibrate the AE sensors 116. For example, an ultrasonic wave can be generated by an artificial source such as impact at a known location or distance away from the AE sensors 116. Preferably, a set of ultrasonic wave velocity measurements shall be taken prior to the commissioning of a new furnace 102. During this stage, an operator can generate impacts at the refractory wall 114 at known locations, from the inside of the furnace 102. The signals can be detected by the AE sensors 116 mounted on the outer surface of the outer shell 108. The velocity model, which will be used for passive AE monitoring, can then, be calculated based on these initial readings, and using a thermal correction factor. The synthetic ultrasonic signals may also be analyzed for their amplitude and frequency range.

Figure 5:
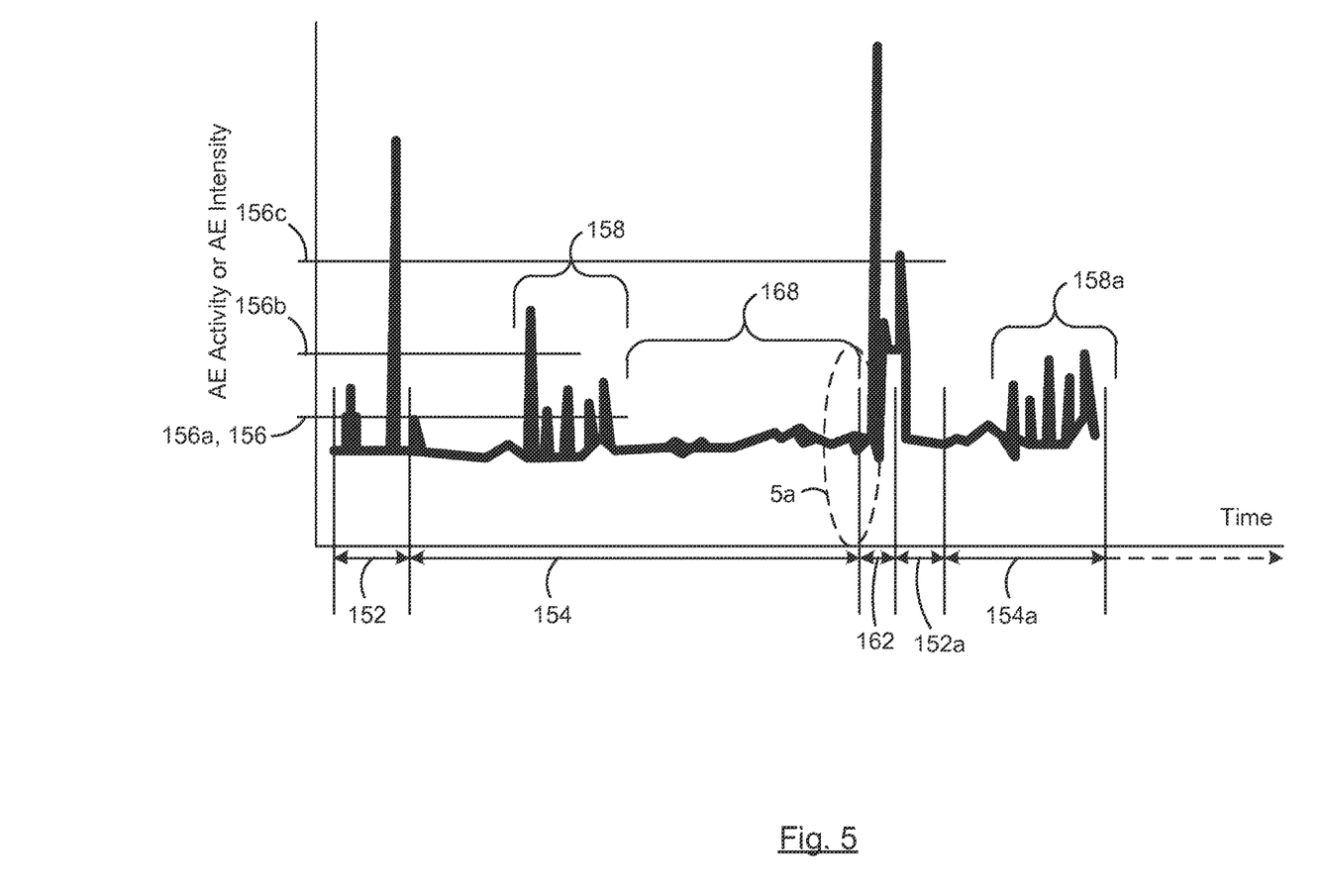
FIG. 5 is a line graph illustrating AE activity in a furnace over time.

Referring to FIG. 5, a line graph illustrates a schematic representation of the AE activity generated by the furnace 102 during operation.

During the start-up phase 152, for example when the furnace is started for the first time, a variety of acoustic emissions may be generated throughout the furnace 102. Some of these emissions may have a relatively high magnitude, as illustrated.

During start-up, increases in operating temperature and ferrostatic pressure exerted by the molten contents of the furnace 102 may cause the outer shell 108 to elastically expand, and may cause some degree of permanent, plastic deformation or stretching of the outer shell 108. During this initial expansion process, a plurality of AE events may be detected by the AE monitoring system 100 as the steel outer shell plastically deforms.

When the furnace reaches a generally steady-state operating phase 154, the outer shell may not experience further plastic deformation, and the number of AE events generated within the outer shell will decrease and/or be substantially eliminated. During such periods of steady state operation, the AE monitoring system 100 may detect little to no AE activity from the outer shell 108. A steady state baseline for acoustic emissions from a given furnace can be determined during this steady-state phase 154 of operation, and an operating threshold AE value 156 can be determined. The threshold AE value may be unique for any given furnace or vessel that is monitored using an AE monitoring system 100. The AE threshold value can be stored in the memory module 142.

Optionally, a plurality of different AE value thresholds can be stored for a given furnace 102. For example, a warning AE threshold value 156a and a higher, alarm AE threshold value 156b can be both be stored for a given furnace 102.

While the furnace 102 is in operation, changes in the operating conditions of the furnace over time may exert additional forces on the outer shell 108, which in some instances may lead to unwanted plastic deformation of the outer shell 108. For example, uncontrolled hearth refractory 112 expansion may cause bulging deformation in the steel outer shell 108 and may cause local separation of the outer shell 108 from the inner refractory materials 110. Separation between the outer shell 108 and the refractory 110 may decrease cooling efficiency and may lead to further damage to the outer shell 108. In other examples, outer shell 108 deformation may be caused by hydration of the refractory bricks 110 (i.e. swelling) beyond the intended design limits. Regions of local outer shell deformation may be prone to failure, which may result in a run-out.

The aggressive thermal and chemical conditions inside the furnace 102, as well as the movement of the molten bath, may also contribute to wearing of the refractory 110. Typically the refractory wear occurs in the hearth 112, near the tapholes, within the walls below the maximum bath level. The wearing of the refractory 110 can affect the structural stability of the furnace by thinning the refractory walls 114. The heat transfer is also affected which may lead to even further deterioration. Also the potential for metal leaks increase due to the thinning of the walls 114, hearth 112 or tapholes.

Any of the above conditions can disrupt the operating conditions of the furnace 102, illustrated as an interruption phase 158, resulting in increased AE activity and/or AE intensity.

If, as illustrated, the AE intensity detected using the AE sensors 116 is compared to and exceeds one or more of the AE threshold values 156, the controller 120 may generate a corresponding output. In the illustrated example, the first AE peak in the interruption phase 158 exceeds the alarm AE threshold value 156b, and may trigger an alarm output from the controller 120 (for example a flashing red light and audible siren). The following four AE peaks in interruption phase 158 (to the right as viewed in FIG. 5) exceed the warning AE threshold 156a, but do not exceed the alarm AE threshold 156b. Detection of these four peaks may result in a warning output from the controller 120 (such as a warning display on a computer screen and a flashing yellow light). When the AE intensity drops below the warning AE threshold, the warning outputs may cease.

Preferably, the AE threshold values 156 are set such that normal operations of the furnace which raise the baseline AE level of the furnace 102, for example a general increase in operating power (illustrated as power increase phase 160), will not trigger a warning or alert output.

Optionally, an emergency or shut-down AE threshold value 156c can be stored in the memory 142. During a severe interruption phase 162 (such as may occur preceding and during a run-out), the AE intensity generated by the furnace 102 may increase significantly. Such an increase may exceed both the warning and alarm AE thresholds 156a, 156b. If the AE intensity reaches the shut-down AE threshold 156c, the controller 120 may be operable to automatically intervene in the operation of the furnace 102. For example, the controller 120 may be configured to automatically reduce the power supplied to the furnace 102 if the AE signals from the furnace exceed the shut-down AE threshold 156c.

Preferably, the AE threshold values 156 are selected so that the AE monitoring system 100 can detect, and optionally locate the source of, AE events within the furnace 102 before the outer shell 108 reaches its failure point. In this configuration, the AE monitoring system 100 can be used to help predict potential points of failure on the outer shell 108 before such failures occur.

Figure 5A:
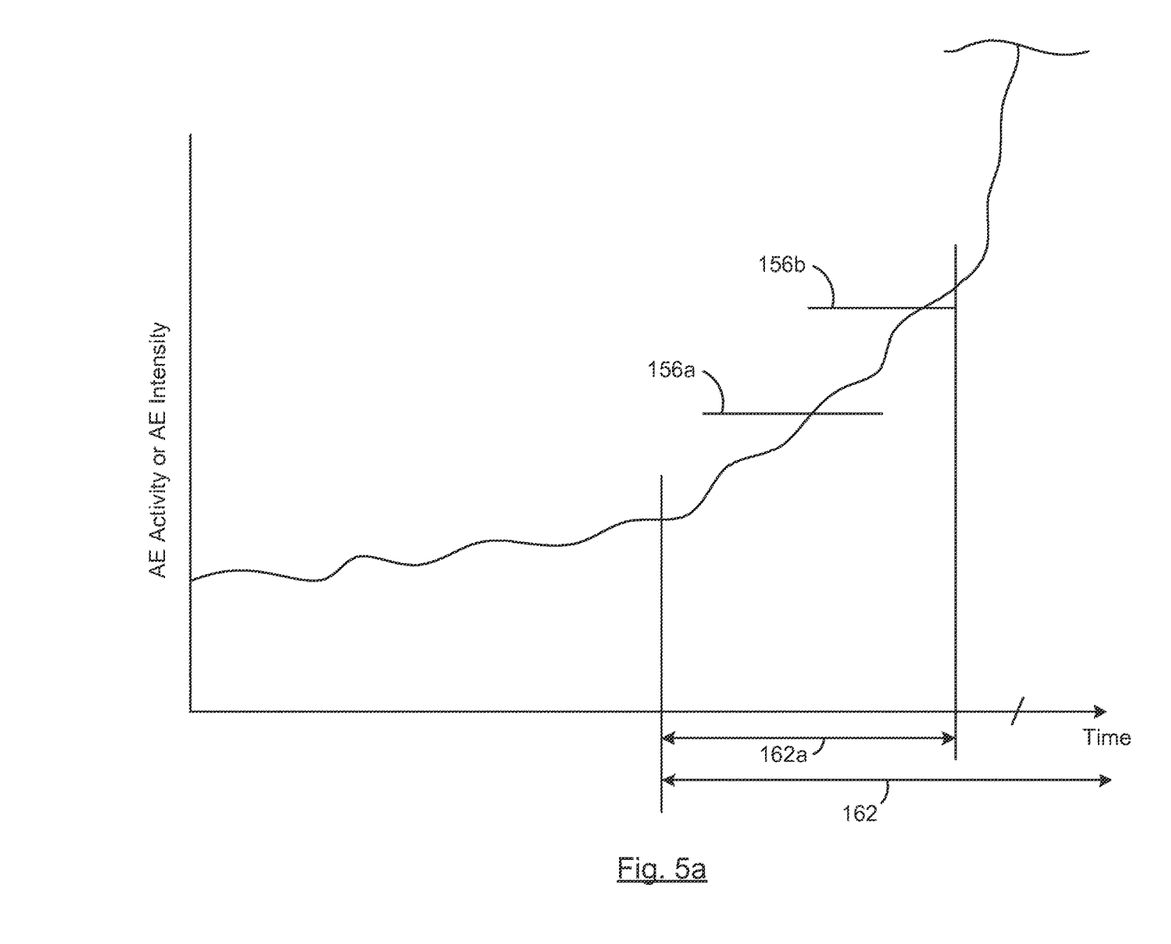
FIG. 5a is an enlarged view of region 5a on FIG. 5.

For example, referring to FIG. 5a, run-out related AE events in the severe interruption phase 162 (which are typically high intensity) may be generated and detected in advance of an actual outer shell 108 rupture. Detection of these lower level pre-cursor AE events, illustrated as a warning phase 162a, may allow a system operator to predict that a run-out (or other such event) is about to occur, and to adjust or shut down the furnace 102 prior to an actual rupture occurring.

If the furnace 102 is subsequently cooled (for example during a shutdown), the outer shell 108 may elastically contract, but may retain a certain degree of plastic deformation. When the furnace 102 is re-heated to substantially the same operating conditions, such as during a subsequent start-up phase 152a, the outer shell 108 may undergo elastic expansion (which does not include the rapid release of energy from within the material and does not generate AE events), but may not undergo any further plastic deformation. During this re-heating phase 152a, the outer shell 108 may not generate AE events that exceed the operating threshold AE values 156 unless, for example, the new thermal expansion exceeds the original amount of thermal expansion.

Figure 6:
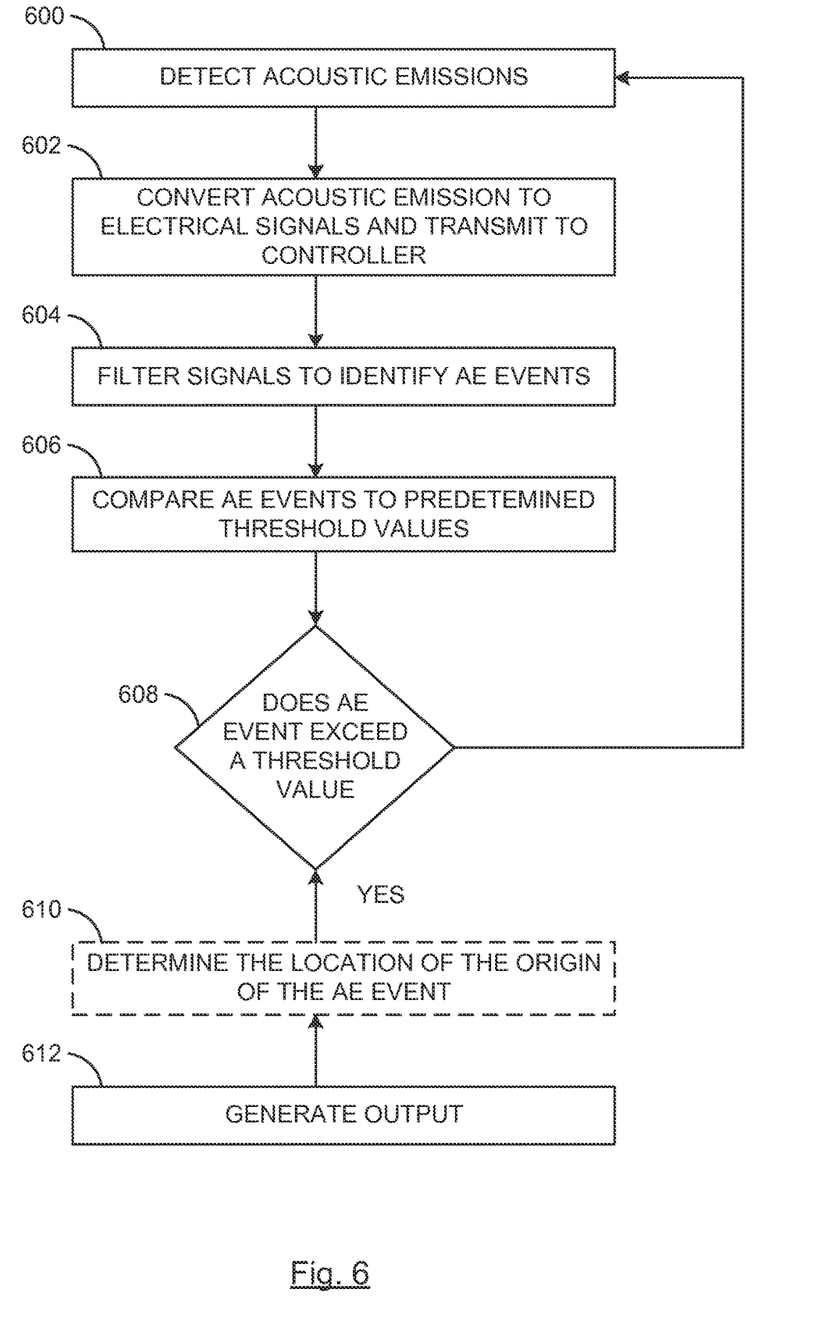
FIG. 6 is a flow chart illustrating a method of operating an AE monitoring system.

Referring to FIG. 6, one method of operating the AE monitoring system 100 includes a step 600 of detecting acoustic emissions from within the furnace 102. At step 602 the acoustic emissions are converted into corresponding electrical signals, and at step 604 the signals are filtered to separate AE events from background noise and normal operating sounds. At step 606 the AE events are compared to one or more predetermined AE threshold values, and at step 608 a query is made to determine if the detected AE event exceeds one or more threshold values 156.

If the AE event does not exceed an AE threshold 156, the method may return to step 600 and continue monitoring the furnace 102. Alternatively, if the AE event does exceed the AE threshold 156, the method may proceed to optional locating step 610 (in which the location of the origin 170 of the AE event is determine) or may proceed directly to step 612, in which an appropriate output signal is generated by the controller 120.

Optionally, the AE monitoring system can be configured to identify the type and severity of the damage (for example cracks) occurring in the outer shell. In such a configuration, the AE events can be assumed to behave like point sources and can be analyzed using a SiGMA procedure (simplified Green's function for moment tensor analysis). Sources of AE events can be classified as tensile or shear cracks by applying the eigenvalue analysis to the moment tensor. The direction of crack propagation can be derived from the eigenvectors.

An example of a mathematical solution of wave motion $u(x, t)$ due to cracking, simplified by using moment tensor $M_{pq}$, is given by Equation 1, where the symbol * represents the convolution integral in time, $b(y)$ represents the crack motion vector, $C_{pqij}$ is the elastic constant, $G_{ip,q}(x, y, t)$ are the spatial derivatives of Green's functions, n is the normal vector to the crack surface, and l is the unit direction vector of the crack motion. $S(t)$ is the source-time function of crack and $\Delta V$ is the crack volume.

$$u_k(x,t)=G_{kp,q}(x,y,t)M_{pq}*S(t)\int_F C_{pqkl}b(y)l_k n_l dF = C_{pqkl}l_k n_l [\int_F b(y)dF] = C_{pqkl}l_k n_l \Delta V = M_{pq} \quad (1)$$

Figure 7:
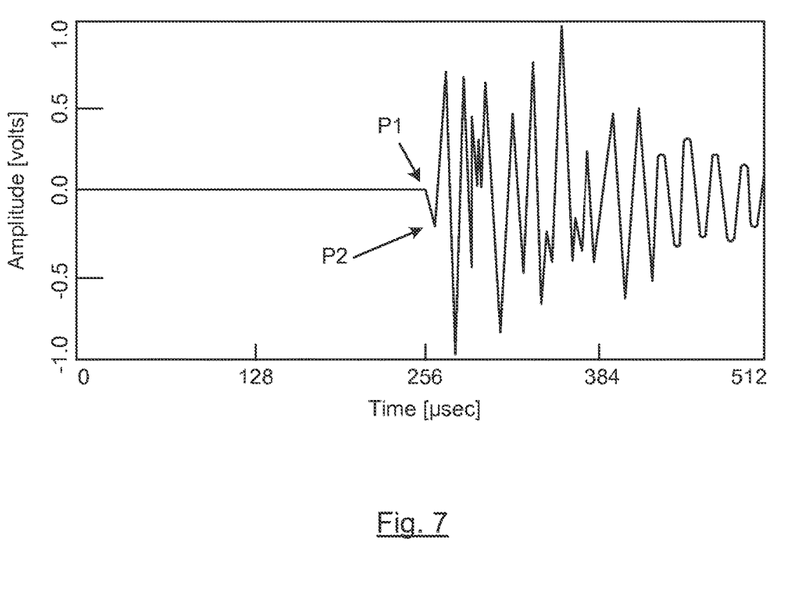
FIG. 7 is line graph illustrating an exemplary AE signal.

From a sample AE waveform as shown in FIG. 7, the arrival time P1 and the first motion amplitude P2 are determined and subjected to further processing. The classification of crack is performed by the eigenvalue analysis of the moment tensor, where X, Y and Z denote the shear ratio, the deviatroic tensile ratio, and the isotropic tensile ratio, respectively. According to the SiGMA procedure, the AE sources are classified based on the following criteria:

X<40% classified as tensile cracks;
40%<x<60% classified as mixed mode cracks;
X>60% classified as shear cracks.

Information regarding the location of the crack, the cracking mode, and the time and rate of occurrence may help facilitate a better understanding of the phenomenon inside the furnace 102 leading the outer shell 108 deformation and failure.

Optionally, the controller 120 may be adapted to communicate with a plurality of other sensors and monitoring devices, including, for example, mechanical strain gauges, optical strain gauges, resistance strain gauges, thermal sensors and topological survey equipment (such as laser scanners). Information from multiple sensors and monitoring devices can be processed to help monitor the structural integrity and other operating characteristics of the furnace 102.

In addition to the embodiments described herein, AE equipment may be adaptable to many forms of production quality control testing, including weld monitoring and leak detection.

The present invention has been described here by way of example only. Various modification and variations may be made to these exemplary embodiments without departing from the spirit and scope of the invention, which is limited only by the appended claims.

The integrity monitoring system can be configured to use a plurality of different types of sensors, either individually or in combination. Suitable types of sensors can include, for example, acoustic sensors, vibration sensors, strain gauges, optical sensors and temperature sensors. In some instances it may be useful to include multiple different types of sensors within an integrity monitoring system to help facilitate the collection of multiple types of data. Optionally, this combination of data can be processed using a common system controller. For simplicity, an example of a structural integrity monitoring system described below is described as having a single type of sensor, however other embodiments of the system may include a plurality of different sensor types.

What is claimed is:

1. An acoustic emission monitoring system for monitoring structural integrity of a furnace having a furnace shell, the system comprising:
   a controller; and
   a plurality of acoustic emission sensors mounted to the furnace shell and in communication with the controller to provide electric signals corresponding to one or more acoustic emissions generated in the furnace to the controller, the plurality of acoustic emission sensors comprising at least three acoustic emission sensors, wherein at least two acoustic emission sensors are vertically offset from each other and at least two acoustic emission sensors are laterally offset from each other, and wherein the vertical offset is smaller than the lateral offset, and wherein an electric signal is registered as an acoustic emission event if detected by a predetermined number of acoustic emission sensors,
   wherein the controller is configured to determine an operating threshold value during steady-state operation of the furnace and determine one or more failure conditions based on the operating threshold value and one or more acoustic emission events,
   wherein the controller includes a location module for estimating a location of origin of the one or more failure conditions, and
   wherein the controller is configured to analyze a moment tensor determined by the controller based on one or more electric signals pertaining to a particular acoustic emission event in order to identify a cracking mode associated with the particular acoustic emission event.

2. The system of claim 1 wherein at least some of the sensors are coupled to the controller through a preamplifier.

3. The system of claim 1 wherein at least some of the sensors are removably mounted to the furnace shell.

4. The system of claim 3 wherein at least some of the sensors are magnetically mounted to the furnace shell.

5. The system of claim 1 wherein at least some of the sensors are permanently mounted.

6. The system of claim 1 wherein at least some of the sensors are mounted to the furnace shell in positions corresponding to one or more furnace components.

7. The system of claim 1 wherein the spacing of at least some of the sensors mounted on the furnace shell is determined by one or more factors selected from the following list of factors: properties of some or all of the sensors; the resolution of some of all of the sensors; the number of sensors used; the location of furnace components; and the size of the furnace.

8. The system of claim 1 wherein at least some of the sensors are sensitive to acoustic emissions having a frequency higher than a selected threshold.

9. The system of claim 1 wherein the controller includes a filtration module to filter the electric signals.

10. The system of claim 9 wherein the filtration module filters out signals below a selected threshold.

11. The system of claim 10 wherein the threshold is selected from the group consisting of: an operating threshold AE value; a warning AE threshold value, an alarm AE threshold value and a shutdown AE threshold value.

12. The system of claim 1 including sensors of different types.

13. The system of claim 1 wherein the controller includes an output module for providing one or more output signal corresponding to the electric signals.

14. The system of claim 13 wherein an output signal is provided when the intensity of AE events detected by at least one of the sensors exceeds a threshold.

15. The system of claim 14 wherein the threshold is selected from the group consisting of: an operating threshold AE value; a warning AE threshold value, an alarm AE threshold value and a shutdown AE threshold value.

16. The system of claim 1 wherein at least one of the output signals is selected from the group consisting of: warning signals, alarm signals, control signals, sensor control signals and feedback signals.

17. The system of claim 1 wherein the controller includes a display apparatus for providing information relating to the electric signals.

18. The system of claim 1, wherein at least some of the acoustic emission sensors are mounted to the furnace shell in a grid pattern, the grid pattern comprising a plurality of rows and a plurality of columns.

19. The system of claim 1, wherein analyzing the moment tensor comprises analyzing the moment tensor according to a SiGMA procedure.

20. The system of claim 19, wherein the cracking mode is classified based on a shear ratio determined by the SiGMA procedure.

21. The system of claim 20 wherein:
   if the shear ratio is less than or equal to 40%, then the cracking mode is classified as a tensile crack mode;
   if the shear ratio is greater than 40% and less than or equal to 60%, then the cracking mode is classified as a mixed mode; and
   if the shear ratio is greater than 60%, then the cracking mode is classified as a shear crack mode.

22. A method of monitoring the structure of a furnace having a furnace shell, the method comprising:
- mounting a plurality of acoustic emission sensors to the furnace shell, wherein the plurality of acoustic emission sensors comprise at least three acoustic emission sensors, wherein at least two acoustic emission sensors are vertically offset from each other and at least two acoustic emission sensors are laterally offset from each other, and wherein the vertical offset is smaller than the lateral offset, and wherein an electric signal is registered as an acoustic emission event if detected by a predetermined number of acoustic emission sensors;
- providing a controller coupled to the plurality of acoustic emission sensors;
- receiving, by the controller, from the plurality of acoustic emissions sensors, electric signals corresponding to one or more acoustic emissions generated in the furnace, wherein an electric signal is registered as an acoustic emission event if detected by a predetermined number of acoustic emission sensors;
- determining, by the controller, an operating threshold value during steady-state operation of the furnace;
- determining, by the controller, one or more failure conditions based on the operating threshold value and one or more acoustic emission events;
- analyzing, by the controller, the electric signals for estimating a location of origin of the one or more failure conditions; and
- analyzing a moment tensor based on one or more electric signals pertaining to a particular acoustic emission event in order to identify a cracking mode associated with the particular acoustic emission event.

23. The method of claim 22 further comprising positioning at least some of the sensors in positions corresponding to one or more furnace components.

24. The method of claim 22 comprising spacing the sensors mounted on the furnace shell based on one or more factors selected from the following list of factors: properties of some or all of the sensors; the resolution of some of all of the sensors; the number of sensors used; the location of furnace components; and the size of the furnace.

25. The method of claim 22 further comprising filtering out acoustic emissions that are identified by fewer than a selected number of the sensors.

26. The method of claim 22 further comprising filtering out acoustic emissions corresponding to normal operating noises of the furnace.

27. The method of claim 22 wherein the controller includes a display apparatus for providing information relating to the electric signals.

28. The method of claim 22 further comprising identifying one or more pre-cursor AE events.

29. The method of claim 22, further comprising mounting at least some of the acoustic emission sensors to the furnace shell in a grid pattern, the grid pattern comprising a plurality of rows and a plurality of columns.

* * * * *